United States Patent
Mineta et al.

[11] Patent Number: 5,939,586
[45] Date of Patent: Aug. 17, 1999

[54] PROCESS FOR THE PRODUCTION OF INTERMEDIATE FOR LIQUID CRYSTAL COMPOUND

[75] Inventors: Hiroshi Mineta; Tomoyuki Yui, both of Tsukuba, Japan

[73] Assignee: Mitsubishi Gas Chemical Company, Inc., Tokyo, Japan

[21] Appl. No.: 08/962,005

[22] Filed: Oct. 31, 1997

[30]  Foreign Application Priority Data

Nov. 1, 1996 [JP] Japan .................................. 8-291378

[51] Int. Cl.$^6$ ............................ C07C 51/58; C07C 69/76
[52] U.S. Cl. .............................................. 562/862; 560/66
[58] Field of Search ................................ 562/862; 560/66

[56]  References Cited

U.S. PATENT DOCUMENTS

| | | |
|---|---|---|
| 2,529,671 | 11/1950 | Bissinger . |
| 5,374,375 | 12/1994 | Yui et al. . |
| 5,378,396 | 1/1995 | Yui et al. . |

FOREIGN PATENT DOCUMENTS

| | | |
|---|---|---|
| 0042530 | 12/1981 | European Pat. Off. . |
| 2282340 | 11/1990 | Japan . |
| 2196617 | 5/1988 | United Kingdom . |

OTHER PUBLICATIONS

CA 106:94104 (1986).

*Primary Examiner*—Paul J. Killos
*Attorney, Agent, or Firm*—Sherman and Shalloway

[57]  ABSTRACT

A process for the production of an intermediate for a liquid crystal compound, which comprises reacting an alkyloxy-biphenylcarboxylic acid with purified thionyl chloride substantially free of sulfuryl chloride, the thionyl chloride being obtained by adding phenol, etc., to thionyl chloride, heating the mixture and distilling the resultant mixture; and a process for the production of a liquid crystal compound from the above intermediate. According to the present invention, thionyl chloride can be easily purified, and a liquid crystal compound having a very high purity can be obtained by the use of the purified thionyl chloride.

7 Claims, 2 Drawing Sheets

PROCESS FOR THE PRODUCTION OF INTERMEDIATE FOR LIQUID CRYSTAL COMPOUND

FIELD OF THE INVENTION

The present invention relates to a process for the production of a high-purity aromatic acid chloride free of a by-product chlorinated in the aromatic ring and suitable for use as an intermediate for the production of a liquid crystal compound, by the use of thionyl chloride which substantially does not contain sulfuryl chloride; and to a process for the production of a remarkably high-purity liquid crystal compound using the above intermediate.

PRIOR ART

Liquid crystal compounds having a variety of structures, including a nematic liquid crystal compound, have been so far proposed. Of these known compounds, the nematic liquid crystal compound is finding its intensive use in liquid crystal displays utilizing the electro-optical properties thereof. Further, ferroelectric liquid crystal compounds and anti-ferroelectric liquid crystal compounds have recently come to be known, and studies have been and are vigorously made to put them to practical use. These liquid crystal compounds have been rapidly increasing in kinds.

In the fields of ferroelectric liquid crystal compounds and anti-ferroelectric liquid crystal compounds, liquid crystal compounds having a variety of structures have come to be known, while most of the liquid crystal compounds have the structure of the formula $R^1$-O-Ph-Ph-COO-Ph-COO-R* (wherein $R^1$ is linear alkyl, Ph is a 1,4-phenylene group and R* is an optically active group), and these compounds are important.

The liquid crystal compounds of the above structure are generally produced through the following steps.

(1) $CH_3COO$-Ph-COOH+$SOCl_2$→$CH_3COO$-Ph-COCl
(2) $CH_3COO$-Ph-COCl+R*OH→$CH_3COO$-Ph-COOR*
(3) $CH_3COO$-Ph-COOR*+(amine)→HO-Ph-COO-R*
(4) $R^1$-O-Ph-Ph-COOH+$SOCl_2$→$R^1$-O-Ph-Ph-COCl
(5) $R^1$-O-Ph-Ph-COCl+HO-Ph-COO-R*→$R^1$-O-Ph-Ph-COO-Ph-COO-R*

In the above formulae, $R^1$ is a linear alkyl group, -Ph- is a 1,4-phenylene group which may be substituted with fluorine on the benzene ring, and R*OH is an optically active alcohol.

The above production scheme will be outlined as follows.

(1) shows the chlorination of p-acetyloxybenzoic acid with thionyl chloride.
(2) shows the formation of an ester by a reaction between benzoic acid chloride obtained in (1) and an optically active alcohol.
(3) shows the deacetylation of the ester compound obtained in (2).
(4) shows the chlorination of an alkyloxybiphenylcarboxylic acid with thionyl chloride.
(5) shows the formation of an end product by a reaction between a phenol compound obtained in (3) and an acid chloride obtained in (4).

In a series of the above reactions, the chlorination of an alkyloxybiphenylcarboxylic acid with thionyl chloride in (4) in particular involves a problem that besides the intended chlorination of a carboxyl group, the chlorination of a biphenyl group takes place.

As described above, in the preparation of an intermediate for the production of a liquid crystal compound of the formula $R^1$-O-Ph-Ph-COO-Ph-COO-R*, thionyl chloride is used for the chlorination of a carboxylic acid.

In general, commercially available thionyl chloride contains sulfuryl chloride.

The content of the sulfuryl chloride in the commercially available thionyl chloride is generally approximately 1.5% by weight when such a sulfuryl chloride is used, a by-product (A) having the following structure is formed together with the intended product.

If the above by-product (A) is not removed, therefore, the liquid crystal compound formed in the above reaction (5) eventually is accompanied by a by-product (B) having the following structure.

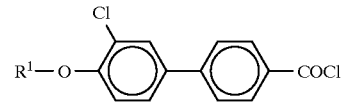

(A)

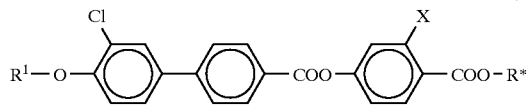

(B)

The intended reaction product in (4) is an acid chloride and very unstable. Further, the reaction product in (4) and the by-product (A) are the same except for the presence of chlorine substituted on a benzene ring, and it is very difficult to separate and purify the reaction product in (4) at this stage.

Further, the liquid crystal compound of the formula (3), which is an end product, to be described later and the above by-product (B) are stable, and they are very difficult to separate from each other efficiently.

The liquid crystal compound of the formula (3) to be described later is generally purified by a column chromatography or liquid chromatography. Since, however, the retention time of the liquid crystal compound (3) and the retention time of the by-product (B) are very close to each other, the efficiency of purification of the end product (liquid crystal compound) is low even if the liquid crystal compound can be separated, and in consequence, this low efficiency causes a problem on economic performance.

In view of the economic performance, therefore, it is desired to prevent the formation of the above by-product (B).

As already discussed, the formation of the by-product (B) is mainly caused due to sulfuryl chloride which is an impurity contained in thionyl chloride. The above problem can be therefore overcome by removing sulfuryl chloride contained in thionyl chloride.

The following methods are known as a method of removing sulfuryl chloride from thionyl chloride.

(i) Triphenyl phosphite is added, followed by distillation.
(ii) Sulfur is added, followed by distillation.
(iii) Diterpene is added, following by distillation.
(iv) Linseed oil is added, followed by distillation.

The above methods have the following problems when used as a method of purifying thionyl chloride to be used for the production of a liquid crystal compound.

(i): Triphenyl phosphite is expensive and the efficiency of removal of sulfuryl chloride is low.
(ii): The efficiency of removal of sulfuryl chloride is low like (i), and the post-treatment is troublesome.

(iii) and (iv): The efficiency of removal of sulfuryl chloride is also low, and thionyl chloride may be re-contaminated by the diterpene or linseed oil with high possibility, and an adverse effect may be caused on the purification of a liquid crystal compound.

The present invention is concerned with a method of easily removing sulfuryl chloride from thionyl chloride to be used for the production of a liquid crystal intermediate; a process for the production of the intermediate by the use of pure thionyl chloride obtained by the above method; and a process for the production of a liquid crystal compound having remarkably high-purity from the above intermediate.

That is, according to the present invention, there is provided a process for the production of an alkyloxybiphenylcarboxylic acid chloride of the following formula (2) as an intermediate for the production of a liquid crystal compound, which comprises reacting an alkyloxybiphenylcarboxylic acid of the following formula (1) with purified thionyl chloride which substantially does not contain sulfuryl chloride,

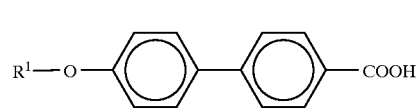
(1)

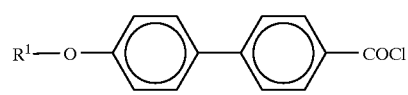
(2)

wherein $R^1$ is a linear alkyl group.

Further, according to the present invention, there is provided a process for the production of a liquid crystal compound of the formula (3), which comprises using the above alkyloxybiphenylcarboxylic acid chloride as an intermediate,

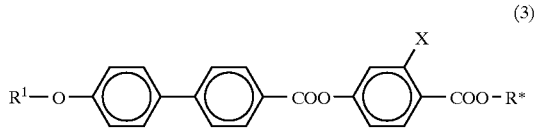
(3)

wherein $R^1$ is a linear alkyl group, X is a hydrogen atom or a fluorine atom, and $R^*$ is an optically active group.

In the liquid crystal compound of the above formula (3), $R^1$ is a linear alkyl group, and the linear alkyl group preferably has 3 to 14 carbon atoms, more preferably 6 to 12 carbon atoms. Further, the optically active group $R^*$ is a group which constitute a essential component in the structural formula of the liquid crystal compound of the formula (3). Typical examples of the optically active group include the following groups (a) to (c).

(a)

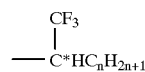

(n is an integer of 4 to 12)

(b)

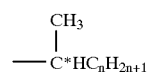

(n is an integer of 3 to 12)

(c)

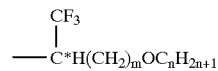

(m is an integer of 2 to 8 and n is an integer of 1 to 4)

In the process of present invention, the term "purified thionyl chloride which substantially does not contain sulfuryl chloride" means that the formation of the by-product (B) is actually not observed when a liquid crystal compound is produced by the use of said purified thionyl chloride. As described above, about 1.5% by weight of sulfuryl chloride can be easily quantitatively determined by analysis, but a very small amount thereof is difficult to determine by a general method.

By the way, the process for the production of the liquid crystal compound of the above formula (3) includes the production of an acid chloride according to the reaction shown in (1) in the explanation of a general production scheme. In this case, however, the formation of a by-product of which the benzene ring is chlorinated is not observed even if thionyl chloride containing sulfuryl chloride is used. That is, in the case of chlorination of p-acetyloxybenzoic acid with thionyl chloride, a by-product of which the benzene ring is chlorinated is actually not formed even if the thionyl chloride contains sulfuryl chloride.

In the present invention, generally, the purified thionyl chloride which substantially does not contain sulfuryl chloride is obtained by adding one compound selected from the group consisting of phenol, cresol, p-hydroxybenzoic acid and aniline to a commercially available thionyl chloride, heating the mixture and then distilling the resulting mixture. Of these compounds, phenol is particularly preferred. The amount of the phenol is preferably 3 to 10 mol % based on the thionyl chloride. The heating is preferably carried out for 1 to 6 hours, and the temperature for the heating is preferably the reflux temperature of thionyl chloride.

Because of the above-explained reason, it is very difficult to analyze the very small content of sulfuryl chloride in the purified thionyl chloride, and it is not easy to determine the allowable amount thereof. In the present invention, however, it is easily determined as a measure, by the following method, whether or not the content of sulfuryl chloride in the purified thionyl chloride is an allowable amount, i.e., whether or not the purified thionyl chloride satisfies the required purity.

That is, a reaction of an alkyloxybiphenylcarboxylic acid of the above formula (1) with purified thionyl chloride is carried out to obtain an alkyloxybiphenylcarboxylic acid chloride of the above formula (2). Then, the resulting acid chloride is reacted with an optically active 4-hydroxybenzoic acid ester according to the above reaction scheme (5) to obtain a liquid crystal compound. When the liquid crystal compound is analyzed by a high pressure liquid chromatography as shown in Examples to be described later, it is found on the basis of a retention time whether or not there is present a by-product formed from the benzene-ring-chlorinated compound of the above formula (2) (e.g., a by-product corresponding to compound B1 in which Y is a chlorine atom in Comparative Example 1). Thus, the purity of the purified thionyl chloride can be judged from the fact that the above by-product is not present.

structure of the formula B1 has a molecular weight of 708, and its peak should appear together with a peak shown by a compound containing an isotope (atomic weight 37) of chlorine of which the presence ratio is about a half and having a molecular weight of 710. In fact, in the mass spectrum in FIG. 2, a main peak M=708 and a peak M+2=710 were observed.

Therefore, the compound which showed a retention time of 5.4 minutes was identified to be the compound (B1) in which Y was a chlorine atom. The compound (B1) was formed in an amount of 16.4% (area ratio) based on the liquid crystal compound as an end product.

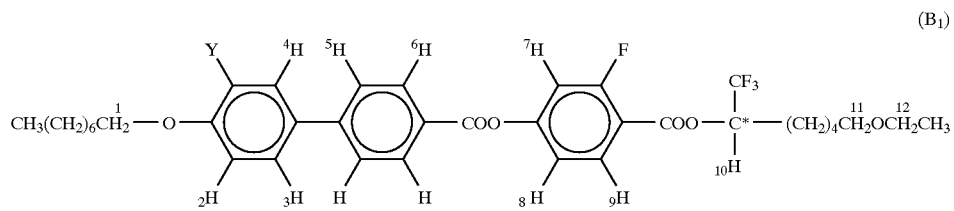

(B1)

In the present invention, thionyl chloride can be easily purified, and a liquid crystal compound having a remarkably high purity can be obtained by the use of the thus purified thionyl chloride.

EXAMPLES

The present invention will be explained with reference to Examples hereinafter, while the present invention shall not be limited thereto.

COMPARATIVE EXAMPLE 1

A large excess of unpurified thionyl chloride for industrial use and 4'-octyloxy-biphenyl-4-carboxylic acid (1 g) were refluxed for 4 hours. A large excess of thionyl chloride was completely removed, and then dichloromethane was added to dissolve a formed acid chloride.

To the above-obtained solution were added 0.7 g of R-(+)-4-hydroxy-2-fluoro-benzoic acid-(1,1,1-trifluoromethyl-6-ethoxy)-hexyl separately prepared and 1.2 g of pyridine, and the mixture was stirred at room temperature for 5 hours.

After termination of the reaction, the reaction mixture was consecutively washed with hydrochloric acid, with an aqueous solution of caustic soda and with water. The solvent was removed, and then the reaction mixture was analyzed by a high pressure chromatography using a silica gel column (solvent: hexane/ethyl acetate=9/1 (volume ratio)).

Figure 1:
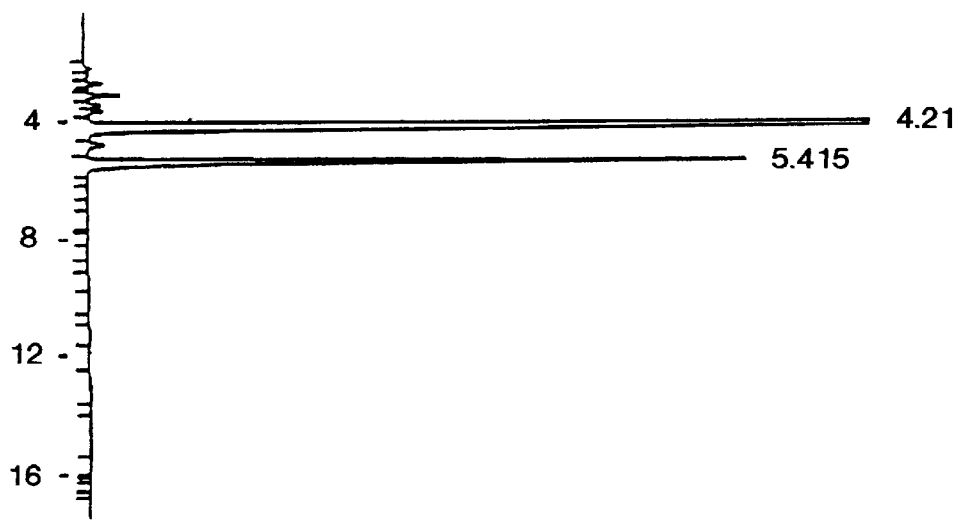
FIG. 1 is a high-pressure liquid chromatogram of a reaction product obtained in Comparative Example 1.

FIG. 1 shows an obtained chromatogram.

In FIG. 1, a peak at a retention time of 4.2 minutes shows an intended liquid crystal compound, and a peak at a retention time of 5.4 minutes shows a by-product. A compound which showed a retention time of 5.4 minutes was collected and analyzed for NMR and mass spectrum.

The above compound had the following chemical formula (B1), and Table 1 shows NMR spectrum of the compound. The NMR data clearly shows that no proton is present in the Y-position.

Figure 2:
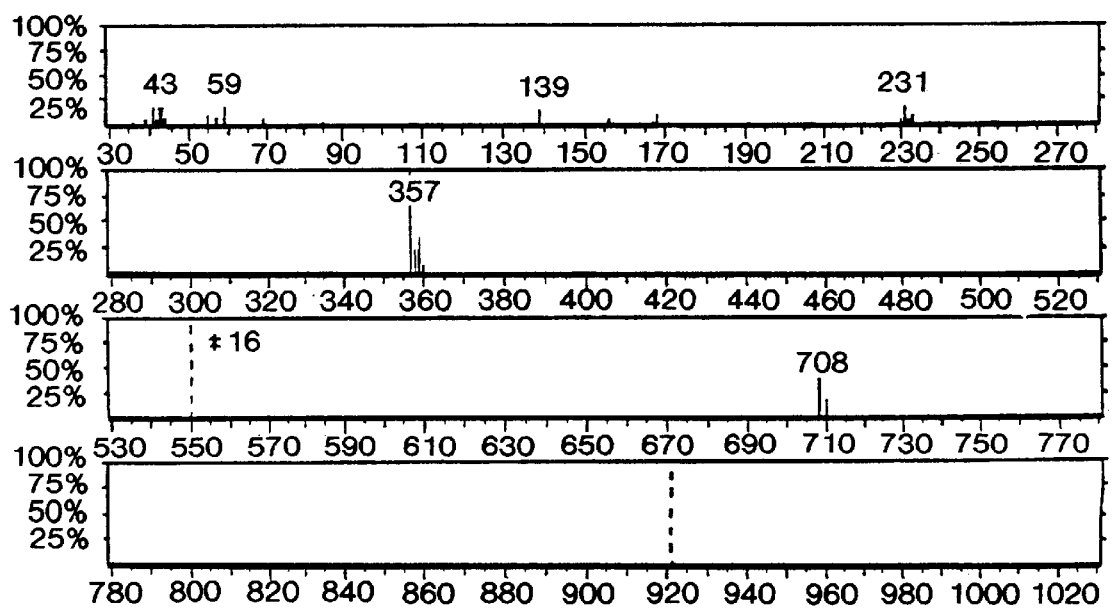
FIG. 2 is a mass spectrum of a by-product formed in Comparative Example 1.

Further, FIG. 2 shows the mass spectrum of the compound.

When Y in the formula (B1) is assumed to be a chlorine atom (atomic weight 35), the compound having the above

TABLE 1

| Proton No. | 1 | 2 | 3 | 4 | 5 | 6 | 7 | 8 | 9 | 10 | 11 | 12 |
|---|---|---|---|---|---|---|---|---|---|---|---|---|
| Chemical shift (ppm) | 4.1 | 7 | 7.5 | 7.7 | 7.7 | 8.2 | 7.2 | 7.2 | 8.1 | 5.6 | 3.4 | 3.4 |

EXAMPLE 1

Phenol (5 mol %) was added to the same thionyl chloride for industrial use as that used in Comparative Example 1, and the mixture was refluxed under heating for 4 hours. Then, the thionyl chloride was distilled by simple distillation. A liquid crystal was synthesized in the same manner as in Comparative Example 1 except that the above-obtained thionyl chloride was used in place.

The reaction product was analyzed by a high pressure liquid chromatography in the same manner as in Comparative Example 1.

Figure 3:
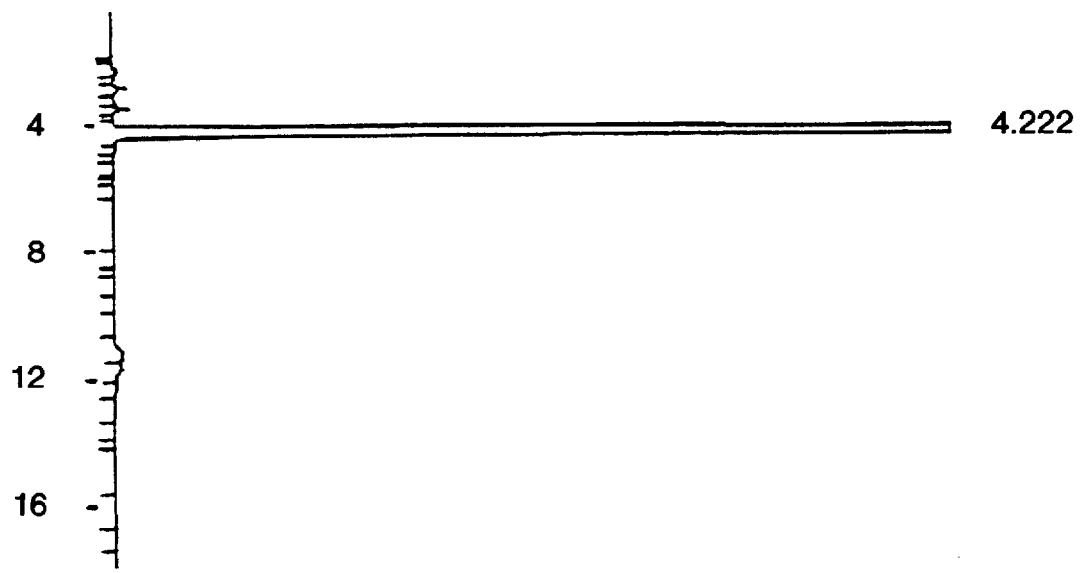
FIG. 3 is a high-pressure liquid chromatogram of a reaction product obtained in Example 1.

FIG. 3 shows the result.

As is clearly shown in FIG. 3, there was found no by-product which showed a retention time of 5.4 minutes.

COMPARATIVE EXAMPLE 2

The same thionyl chloride for industrial use as that used in Comparative Example 1 was purified under the same conditions as those in Example 1 except that the phenol was replaced with triphenyl phosphate. Then, a liquid crystal compound was synthesized in the same manner as in Example 1.

The reaction product was analyzed by a high pressure liquid chromatography in the same manner as in Comparative Example 1, to show the formation of a chlorine compound in an amount of 5.6% based on the liquid crystal compound as an end product.

That is, the amount of the by-product was small as compared with the counterpart in Comparative Example 1. Unlike Example 1, however, the formation of the by-product was not completely prevented.

What is claimed is:

1. A process for the production of an alkyloxybiphenyl-carboxylic acid chloride of the following formula (2) as an intermediate for a liquid crystal compound, which comprises reacting an alkyloxybiphenylcarboxylic acid of the following formula (1) with purified thionyl chloride which substantially does not contain sulfuryl chloride,

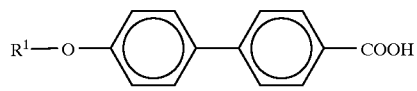

(1)

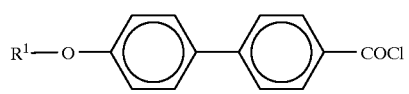

(2)

wherein R¹ is a linear alkyl group.

2. The process of claim 1, wherein the purified thionyl chloride is a product which is obtained by adding at least one component selected from the group consisting of phenol, cresol, p-hydroxybenzoic acid and aniline to thionyl chloride containing sulfuryl chloride as an impurity, heating the mixture, and then distilling the resulting mixture.

3. The process of claim 2, wherein the component added is phenol.

4. The process of claim 2 or 3, wherein the component is added in an amount of 3 to 10 mol % based on the thionyl chloride.

5. The process of claim 2, wherein the heating is carried out for 1 to 6 hours.

6. The process of claim 2, wherein the heating is carried out at the reflux temperature of thionyl chloride.

7. A process for the production of a liquid crystal compound of the following formula (3), characterized by using, as a raw material, the alkyloxybiphenylcarboxylic acid chloride obtained by the process recited in claim 1,

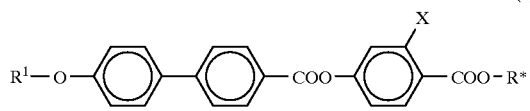

(3)

wherein R¹ is a linear alkyl group, X is a hydrogen atom or a fluorine atom, and R* is an optically active group.

* * * * *